United States Patent
Wang et al.

(10) Patent No.: US 6,673,592 B1
(45) Date of Patent: Jan. 6, 2004

(54) CONTINUOUS CULTIVATION OF MICROORGANISMS IN LARGE OPEN TANKS IN SUNLIGHT

(75) Inventors: Jaw-Kai Wang, 455 Anolani St., Honolulu, HI (US) 96821-2032; Tim Hering, 1671 Kalakaua Ave., #104, Honolulu, HI (US) 96826

(73) Assignees: Jaw-Kai Wang; Tim Hering

( * ) Notice: Subject to any disclaimer, the term of this patent is extended or adjusted under 35 U.S.C. 154(b) by 0 days.

(21) Appl. No.: 08/734,184

(22) Filed: Oct. 21, 1996

(51) Int. Cl.⁷ .................. C12M 1/00; C12M 3/00; C12N 1/12
(52) U.S. Cl. ................ 435/257.1; 435/283.1; 435/289.1; 435/292.1; 435/298.1
(58) Field of Search .................. 435/257.1, 946, 435/283.1, 289.1, 292.1, 298.1

(56) References Cited

U.S. PATENT DOCUMENTS

| | | | |
|---|---|---|---|
| 3,403,471 A | 10/1968 | Clement et al. | 47/1.4 |
| 3,444,647 A | 5/1969 | Takahashi | 47/1.4 |
| 3,650,068 A | 3/1972 | Meyer et al. | 47/1.4 |
| 4,417,415 A | 11/1983 | Cysewski et al. | 47/1.4 |
| 4,869,017 A | 9/1989 | Bird et al. | 47/1.4 |
| 5,121,708 A | 6/1992 | Nuttle | 119/3 |
| 5,661,017 A | * 8/1997 | Dunahay et al. | 435/172.3 |

OTHER PUBLICATIONS

Timmons et al., "Aquacultural Engineering and Waste Management", Proceedings from the Aquaculture Expo VIII & Aquaculture in the Mid–Atlantic Conference, Washington, D.C. (Jun. 24–28, 1995).

* cited by examiner

Primary Examiner—David M. Naff
Assistant Examiner—Deborah K. Ware
(74) Attorney, Agent, or Firm—James Creighton Wray; Meera P. Narasimhan

(57) ABSTRACT

An open, continuous system for culturing Chaetoceros sp. microalgae includes a large outdoor container and full strength sunlight as a light source. The container is preferably a fiberglass tank having an open top, a diameter of approximately 18 inches, and a height of about 5 feet. The container holds a culture medium having the following characteristics: a carbon dioxide controlled pH of about 8.2, a starting nitrogen concentration of at least 3.0 mg N/liter, a starting phosphorous concentration of at least 2.75 mg P/liter, a starting vitamin $B_{12}$ concentration of at least 5 micrograms/liter, a starting iron chloride concentration of at least 0.3 mg/liter, a starting copper sulfate concentration of at least 0.01 mg/liter, a starting silicate concentration of at least 10 mg $SiO_2$/liter, and a $Na_2EDTA$ concentration of 5 mg/liter. The medium is inoculated with a seed stock of Chaetoceros sp. microalgae and exposed direct sunlight. A portion of the cultured microalgae, preferably in the 90% range, is harvested each day and replaced with new culture media. As sterile conditions are not required, seawater may be used as the replacing culture media.

8 Claims, 1 Drawing Sheet

FIG. 1
FIG. 2
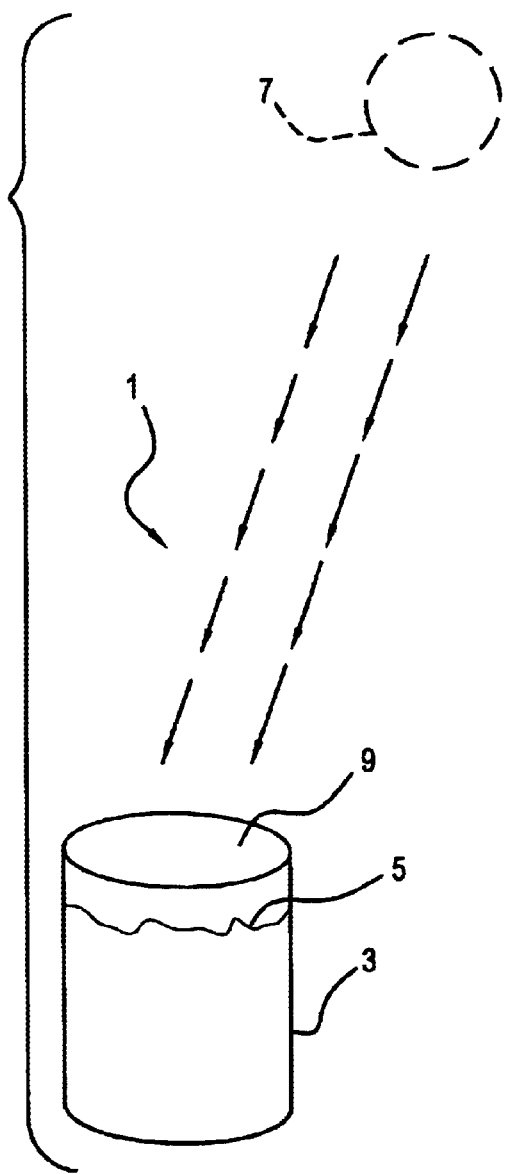
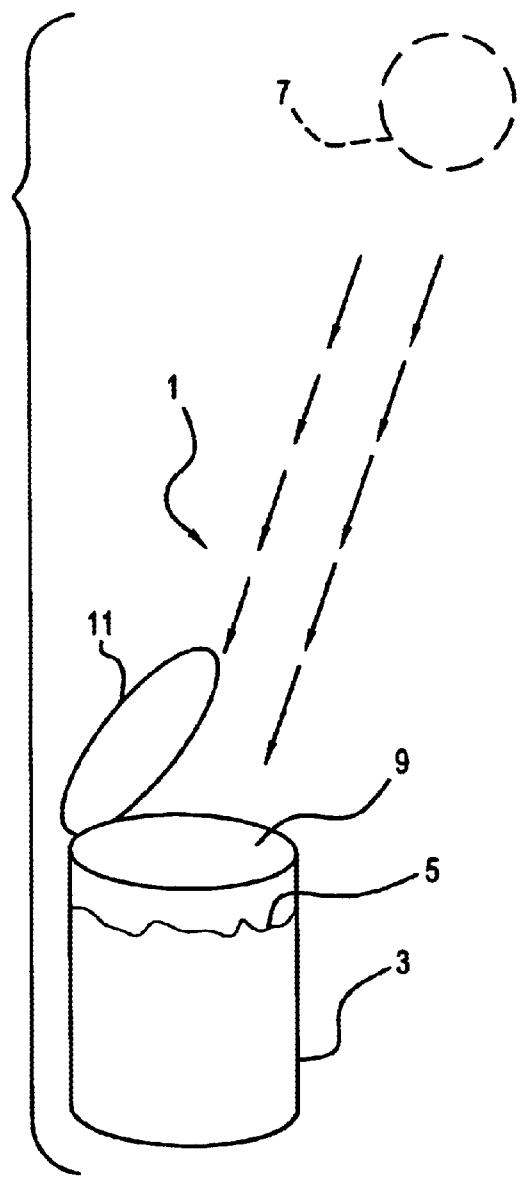

CONTINUOUS CULTIVATION OF MICROORGANISMS IN LARGE OPEN TANKS IN SUNLIGHT

BACKGROUND OF THE INVENTION

The present invention relates to microalgae culture systems.

Microalgae and seaweed are valuable aquaculture crops, as they remain prominent in the culture of many aquatic animals, especially marine species. In particular, microalgae production is extremely important to the successful production of seed stock in the marine shrimp farming industry and in the bivalve farming industry. Many species of fish consume algae as adults and receive indirect benefits of algae in their tanks. In addition, the intensive larviculture of many species of marine fish depend on large supplies of rotifers, which are generally raised on microalgae. Needs exist for cost and time efficient systems for culturing microalgae on a consistent and reliable basis.

Current methods for culturing phytoplankton are of three basic types: continuous, semi-continuous and batch. Continuous cultures are steady-state continuous flow cultures in which the rate of growth is governed by the rate of supply of the limiting nutrient. Continuous culture systems are generally delicately balanced, often axenic, are harvested continually and receive constant nutrient replenishment. The rate of washout in continuous culture systems must be adjusted such that the rate of harvest is slightly slower than the maximum specific growth rate. While continuous cultures are efficient and provide for a consistent supply of high-quality cells, existing continuous culture systems are only feasible for the production of relatively small amounts of microalgae.

Semi-continuous cultures and batch cultures are used when large quantities of algal biomass are required. In semi-continuous cultures, a given population is allowed to grow until a desired cell density is achieved, at which time the culture is partially harvested and a fresh medium is added. The culture is repeatedly grown up and harvested. Semi-continuous cultures are mainly indoors, as outdoor conditions render the duration of the culture unpredictable. Competitors, other contaminants and predators eventually build up, rendering the culture inviable. Cells produced using semi-continuous culture systems tend to vary in nutritional quality.

Batch cultures differ from continuous and semi-continuous systems in the area of harvesting. In batch cultures, when the population reaches its maximum or near-maximum density, the culture is completely harvested. Batch cultures are extremely inefficient and often result in inconsistent quality.

Needs exist for microalgae culture systems that have the production capabilities of batch or semi-continuous systems and the consistency and efficiency of continuous systems.

Compounds which are active against several drug resistant pathogenic bacteria have been isolated from the Chaetoceros sp. microalgae. Needs exist for methods and systems for producing mass quantities of Chaetoceros sp. microalgae for use in developing antibiotics.

*Vibrio vulnificus* contamination is currently a major problem facing the oyster farming industry. The U.S. Food and Drug Administration has recently banned oyster harvests from the Gulf of Mexico during the summer months due to *Vibrio vulnificus* contamination of the oysters. Studies demonstrate that Chaetoceros sp. microalgae is active in vitro against pathogenic *Vibrio vulnificus*. Needs exist for mass cultivating methods that allow for oyster depuration systems that take advantage of Chaetoceros sp. activity against *Vibrio vulnificus* to cleanse the oysters of that pathogen.

Existing methods for mass cultivating Chaetoceros sp. and other microalgae have proven inadequate. The primary difficulty in culturing Chaetoceros sp. microalgae is that undesirable species contaminate and outcompete Chaetoceros sp. microalgae in culture vessels and outdoor algal systems. Costly water treatment systems are necessary in existing system to filter out predators, competitors and disease from the culture media before the media is used to culture the microalgae.

Existing indoor and outdoor microalgae culture systems are unacceptable. Existing indoor cultures produce small volumes of algae under controlled conditions. Illumination, temperature and nutrient levels are controlled within strict levels, allowing for predictable growth. Early stages of existing large outdoor unialgal cultures are generally grown indoors. Many indoor closed cultures are axenic, or free of foreign organisms such as bacteria. However, axenic cultures require scrupulously sterilized glassware, tubing, water, pipettes, nutrient, media, etc. to avoid contamination. While axenic cultures are less prone to failure than outdoor systems, they are prohibitively expensive for commercial operations for producing large volumes of microalgae.

In efforts to limit contamination and predation, many existing methods include a scaling up process, whereby small, test tube cultures are gradually transferred to larger culture vessels having the desired harvest volume. That process often takes upwards of two weeks to complete, is labor intensive, and must be conducted in sterile rooms with artificial lighting and cooling to avoid contamination by competing microalgae species.

Needs exist for relatively inexpensive, non-labor intensive methods and system for mass cultivating Chaetoceros sp. microalgae.

SUMMARY OF TEE INVENTION

The present invention is an open, continuous microalgae culture system that optimizes culture conditions for microalgae, such as Chaetoceros sp. marine microalgae, in a cost effective manner. The system provides for faster and more efficient microalgae culturing than existing methods and systems. In the present invention, Chaetoceros sp. exemplifies the microalgae culture system and is not limited to that species alone.

In contrast to the widely used indoor cultivation systems described in the background, the present system establishes optimal culture conditions for Chaetoceros sp. microalgae and provides for the outdoor culturing of the microalgae. No water treatment systems are needed as the Chaetoceros sp. microalgae outcompetes other species of microalgae in the culture. The present invention provides for the continuous mass cultivation of Chaetoceros sp. microalgae in large outdoor containers using natural sunlight. By harvesting a portion of the culture periodically (i.e., each day) and replacing the harvested volume with new, non-sterile culture media such as seawater, the present system incurs no "down time" and allows for the continuous production of Chaetoceros sp. microalgae in mass quantities. Labor, utility and equipment expenses are minimized in the present system, as sterile conditions and artificial culturing apparatus are not required.

Advantages realized by the present open Chaetoceros sp. microalgae system include:

low initial capital expenses small land area requirements minimal labor requirements low electricity requirements a sterile room is not needed to store test tube cultures of pure strain single species Chaetoceros sp. microalgae a single outdoor tank is included.

The initial capital expenses and the land use are much less than in existing systems since just a single, unprotected outdoor tank produces what in traditional algal culture requires a series of indoor protected tanks, an artificial light source, a sterilized water source and a sterile culture room for test tube cultures. Labor savings result from not having to transfer the cultures into a series of larger tanks as well as not having to maintain test tube cultures of Chaetoceros sp. microalgae.

The present culture system and method have immediate applications in marine shrimp hatcheries, bivalve hatcheries and oyster depuration facilities. The present invention provides for the enhancement of the aquaculture industry by providing high quality protein to seed stock, oysters, shrimp and prawns. Seed stock and broodstock produced using the present system provides a valuable resource for revitalizing disease-threatened oyster and marine shrimp farms.

The present invention is a method for the continuous culturing of microalgae. The steps of the present method include providing a single container, providing a culture medium having an aqueous medium and a seed stock of the microalgae in the container, exposing the culture medium to light, maintaining the pH of the culture medium at a fixed level, harvesting a percentage of the culture medium at a duration of a predetermined period and adding a replacement seed stock medium to an unharvested portion of the medium. The step of providing a culture medium includes establishing optimal culture concentrations of constituent elements of the aqueous medium. The constituent elements include, but may not be limited to, nitrogen, phosphorous, vitamin $B_{12}$, iron chloride, copper sulfate, silicate and $Na_2EDTA$. The starting concentrations of at least one of the constituent elements is established at an optimal level. In preferred embodiments, the microalgae is Chaetoceros sp. microalgae and the constituent elements of the aqueous medium have a starting nitrogen concentration of at least about 3.0 mg N/liter, a starting phosphorous concentration of at least about 2.75 mg P/liter, a starting vitamin $B_{12}$ concentration of at least 5 about micrograms/liter, a starting iron chloride concentration of at least about 0.3 mg/liter, a starting copper sulfate concentration of at least about 0.01 mg/liter, a starting silicate concentration of at least about 10 mg $SiO_2$/liter, and a $Na_2EDTA$ concentration of about 5 mg/liter. The pH of the medium is preferably maintained at a fixed level of about 8.2. In one preferred embodiment, the pH level is maintained by introducing carbon dioxide to the medium.

Preferably, about 90% of the culture medium is harvested each period. The harvested portion is replaced with seed stock of microalgae, which is preferably seawater. A preferable harvesting period is about twenty-four hours.

The culture medium is preferably exposed to full strength direct sunlight.

Preferably, the single container is a tank having an open top. In preferred embodiments, the tank is generally cylindrical, has a diameter of about 18 inches and a height of about five feet, and is made of fiberglass.

A culture medium for growing Chaetoceros sp. microalgae preferably includes a starting nitrogen concentration of at least about 3.0 mg N/liter, a starting phosphorous concentration of at least about 2.75 mg P/liter, a starting vitamin $B_{12}$ concentration of at least about 5 micrograms/liter, a starting iron chloride concentration of at least about 0.3 mg/liter, a starting copper sulfate concentration of at least about 0.01 mg/liter, a starting silicate concentration of at least about 10 mg $SiO_2$/liter, and a $Na_2EDTA$ concentration of about 5 mg/liter, and wherein the medium has a pH maintained at a fixed level of about 8.2.

An open, continuous marine microalgae culture system includes a container, a culture medium positioned in the container and a light source for directing light rays to the culture medium in the container. The culture medium further includes an initial aqueous medium and a seed stock of microalgae. The aqueous medium further includes starting constituent element concentrations that are optimal for growing the microalgae. A harvester for removing a percentage of grown microalgae from the culture medium may also be included.

These and further and other objects and features of the invention are apparent in the disclosure, which includes the above and ongoing written specification, with the claims and the drawings.

BRIEF DESCRIPTION OF THE DRAWINGS

FIG. 1 is a schematic illustration of the present system.

FIG. 2 is a schematic illustration of the present system including a container having a cover.

DETAILED DESCRIPTION OF THE PREFERRED EMBODIMENTS

As shown in the drawings, the present invention is an open, continuous system 1 for culturing microalgae, including, for example, Chaetoceros sp. microalgae. The system includes a container 3 for holding a culture medium 5. The culture medium 5 includes an initial aqueous solution and a seed stock of microalgae. The initial aqueous solution is prepared such that optimal conditions for culturing microalgae of interest are established. Once the optimal conditions are established, the aqueous solution is inoculated with a seed stock of microalgae. The resulting culture medium 5 is pH controlled in a set range, preferably using carbon dioxide additions. A light source 7, preferably the sun, delivers light and heat to the culture medium 5, facilitating the growth of the microalgae culture. Periodically, a percentage of the microalgae culture medium is harvested. The harvested medium is replaced with a non-sterile medium, such as seawater. The method is continually repeated, thereby providing for uninterrupted harvests.

Optimal conditions for culturing a selected microalgae must be established in the aqueous medium. Optimal conditions are those that allow a seed stock of microalgae to grow and outcompete predators, contaminants and other potential scavengers. Creating such a medium allows for the mass production of microalgae outdoors and under non-sterile conditions. Preferably, optimal conditions are attained in the aqueous medium by initially adjusting the concentrations of some or all of the following constituents: nitrogen, phosphorous, vitamin $B_{12}$, iron chloride, copper sulfate, silicate and $Na_2EDTA$. The pH of the culture medium is continuously monitored, with adjustments, such as carbon dioxide treatments, performed to maintain the pH at a desired level.

In a preferred embodiment, the present system is used for culturing Chaetoceros sp. microalgae. The container holds an aqueous medium having the following starting characteristics: a carbon dioxide controlled pH of about 8.2, a starting nitrogen concentration of at least 3.0 mg N/liter, a starting phosphorous concentration of at least 2.75 mg P/liter, a starting vitamin $B_{12}$ concentration of at least 5 micrograms/liter, a starting iron chloride concentration of at least 0.3 mg/liter, a starting copper sulfate concentration of at least 0.01 mg/liter, a starting silicate concentration of at least 10 mg $SiO_2$/liter, and a $Na_2EDTA$ concentration of 5 mg/liter. The medium is inoculated with a seed stock of Chaetoceros sp. microalgae and exposed to direct sunlight. The microalgae grows in the open environment and is periodically and continuously harvested. The harvested volume is replaced with a new seed stock of Chaetoceros sp. microalgae and culturing is repeated.

While any light source may be used in the present system, culturing the microalgae under full strength sunlight is the most economical option.

A percentage of the culture is periodically harvested. Preferably, about 80% of the culture volume is harvested at the conclusion of each period. In preferred embodiments of the present system and method, the culture is harvested once a day, or approximately once every twenty-four hours. As non-sterile conditions are not required, the harvested volume is readily replaced with non-sterile seed stock of microalgae, such as seawater. The volume is preferably manually harvested or harvested using any acceptable harvesting machine or apparatus.

The container 3, which may have any acceptable dimensions and be constructed of any acceptable material, preferably has an open top 9. As shown in FIG. 2, a transparent, light-passing cover 11 may be positioned over the open top 9. In one embodiment, the cover 11 is removably positioned over the open top 9. In another preferred embodiment, the cover 11 is hinged or otherwise connected to a side of the container 3 for movably overlying the open top. The cover 11 may also permanently overly the open top 9. In those embodiments, the cover 11 or body of the container 3 has at least one opening for allowing harvesting of the culture and replacing the harvested volume with new culture media.

In preferred embodiments, the container 3 is a fiberglass tank having an open top 9. In one preferred embodiment, the tank is cylindrical in shape, has a diameter of about 18 inches and a height of about five feet.

By culturing microalgae in the optimal conditions, the production of large quantities of microalgae are possible in a cost effective manner. A single container is situated in an outdoor environment such that the contents of the container are directly exposed to natural light. No artificial light sources or additional transfer tanks are needed. Contaminants and predators are not a problem, as the established media conditions allow the microalgae to outcompete and overcome unwanted or detrimental species.

By establishing the optimal culture conditions for Chaetoceros sp. microalgae, the present system provides for an environment where Chaetoceros sp. microalgae outcompetes other species of microalgae from the culture. That enables Chaetoceros sp. microalgae to be cultured continuously in large, outdoor containers using natural light. The need for labor intensive and costly systems designed to exclude other species from the culture is eliminated. The use of natural light greatly decreases the costs and problems associated with artificial lights. In addition, the Chaetoceros sp. seed stock is obtained by adding a bucket of seawater from the nearest seashore to the culture media, thereby eliminating the expense of sterile clean rooms for storing test tube cultures of Chaetoceros sp. microalgae.

While the invention has been described with reference to specific embodiments, modifications and variations of the invention may be constructed without departing from the scope of the invention, which is defined in the following claims.

We claim:

1. A method for continuous culturing of microalgae comprising the steps of providing an open container, providing a culture medium having an aqueous medium and a seed stock of the microalgae in the container, exposing the culture medium to light, maintaining a pH of the culture medium at a fixed level, harvesting a portion of the culture medium at a duration after a predetermined period and adding a replacement seed stock medium to an unharvested portion of the medium, wherein the providing a culture medium step further comprises the step of establishing concentrations of constituent elements in the aqueous medium for unialgal harvesting for promoting optimum growth rates of the microalgae, wherein the container is a tank having an open top, wherein the tank is generally cylindrical having a diameter of about 18 inches and a height of about five feet, and the tank is made of fiberglass material.

2. The method of claim 1, wherein the constituent elements comprise nitrogen, phosphorous, vitamin $B_{12}$, iron chloride, copper sulfate, silicate and $NA_2EDTA$, and wherein starting concentrations of at least one of the constituent elements is established at an optimal level.

3. The method of claim 2, wherein the microalgae is Chaetoceros sp. microalgae, wherein the constituent elements of the aqueous medium further comprise a starting nitrogen concentration of at least about 3.0 mg N/liter, a starting phosphorous concentration of at least about 2.75 mg P/liter, a starting vitamin $B_{12}$ concentration of at least about 5 micrograms/liter, a starting iron chloride concentration of at least about 0.3 mg/liter, a starting copper sulfate concentration of at least about 0.01 mg/liter, a starting silicate concentration of at least about 10 mg $SiO_2$/liter, and a $Na_2EDTA$ concentration of about 5 mg/liter, and wherein the maintaining the pH step comprises maintaining a pH about 8.2.

4. The method of claim 1, wherein the harvesting step comprises removing about 90% of the culture medium.

5. The method of claim 1, wherein the seed stock of microalgae is seawater.

6. The method of claim 1, wherein the exposing step comprises exposing the culture medium to direct sunlight.

7. The method of claim 1, wherein the maintaining step further comprises adding carbon dioxide to the culture medium.

8. The method of claim 1, wherein the predetermined period is about twenty-four hours.

* * * * *

UNITED STATES PATENT AND TRADEMARK OFFICE
CERTIFICATE OF CORRECTION

PATENT NO. : 6,673,592 B1  
DATED : January 6, 2004  
INVENTOR(S) : Wang et al.

Page 1 of 1

It is certified that error appears in the above-identified patent and that said Letters Patent is hereby corrected as shown below:

<u>Title page,</u>
Item [*] Notice, should read:

-- Subject to any disclaimer, the term of this patent is extended or adjusted under 35 U.S.C. 154(b) by 1032 days. --

Signed and Sealed this

Eighteenth Day of May, 2004

JON W. DUDAS  
*Acting Director of the United States Patent and Trademark Office*